(12) United States Patent
Kusumoto

(10) Patent No.: US 8,660,667 B1
(45) Date of Patent: Feb. 25, 2014

(54) STYLETLESS CARDIAC LEAD EXTRACTION WITH ROLLING TRACTION HANDLE

(76) Inventor: Walter Kusumoto, Chico, CA (US)

( * ) Notice: Subject to any disclaimer, the term of this patent is extended or adjusted under 35 U.S.C. 154(b) by 495 days.

(21) Appl. No.: 12/804,688

(22) Filed: Jul. 27, 2010

Related U.S. Application Data

(60) Provisional application No. 61/271,924, filed on Jul. 28, 2009, provisional application No. 61/276,372, filed on Sep. 10, 2009.

(51) Int. Cl.
*A61N 1/00* (2006.01)
(52) U.S. Cl.
USPC ........................................ 607/122
(58) Field of Classification Search
USPC ................................ 607/116–138
See application file for complete search history.

(56) References Cited

U.S. PATENT DOCUMENTS

| 4,471,777 A * | 9/1984 | McCorkle, Jr. ............... 606/129 |
| 2001/0000349 A1 * | 4/2001 | Coe et al. ...................... 607/119 |

* cited by examiner

*Primary Examiner* — Eric D. Bertram
*Assistant Examiner* — Elizabeth K So
(74) *Attorney, Agent, or Firm* — Heisler & Associates

(57) ABSTRACT

A cardiac lead extraction system is described that is styletless in nature. A cord is provided having at least one crimping bead or other deformable mass thereon. A wire associated with the lead, such as an inner wire thereof is exposed. The crimping bead on the cord is then brought adjacent the wire and crimped onto the wire. Preferably, multiple crimping beads are used for securing the cord at multiple places to the wire. The cord can also be looped and crimped back on itself. Tension is then applied to the cord and correspondingly to the lead. An extraction sheath can then be advanced over a cover of the lead to separate it from adjacent body tissues before lead removal. A traction handle allows a distal end of the cord to be readily held and tensioned by a medical practitioner, especially while advancing the extraction sheath over the lead.

9 Claims, 4 Drawing Sheets

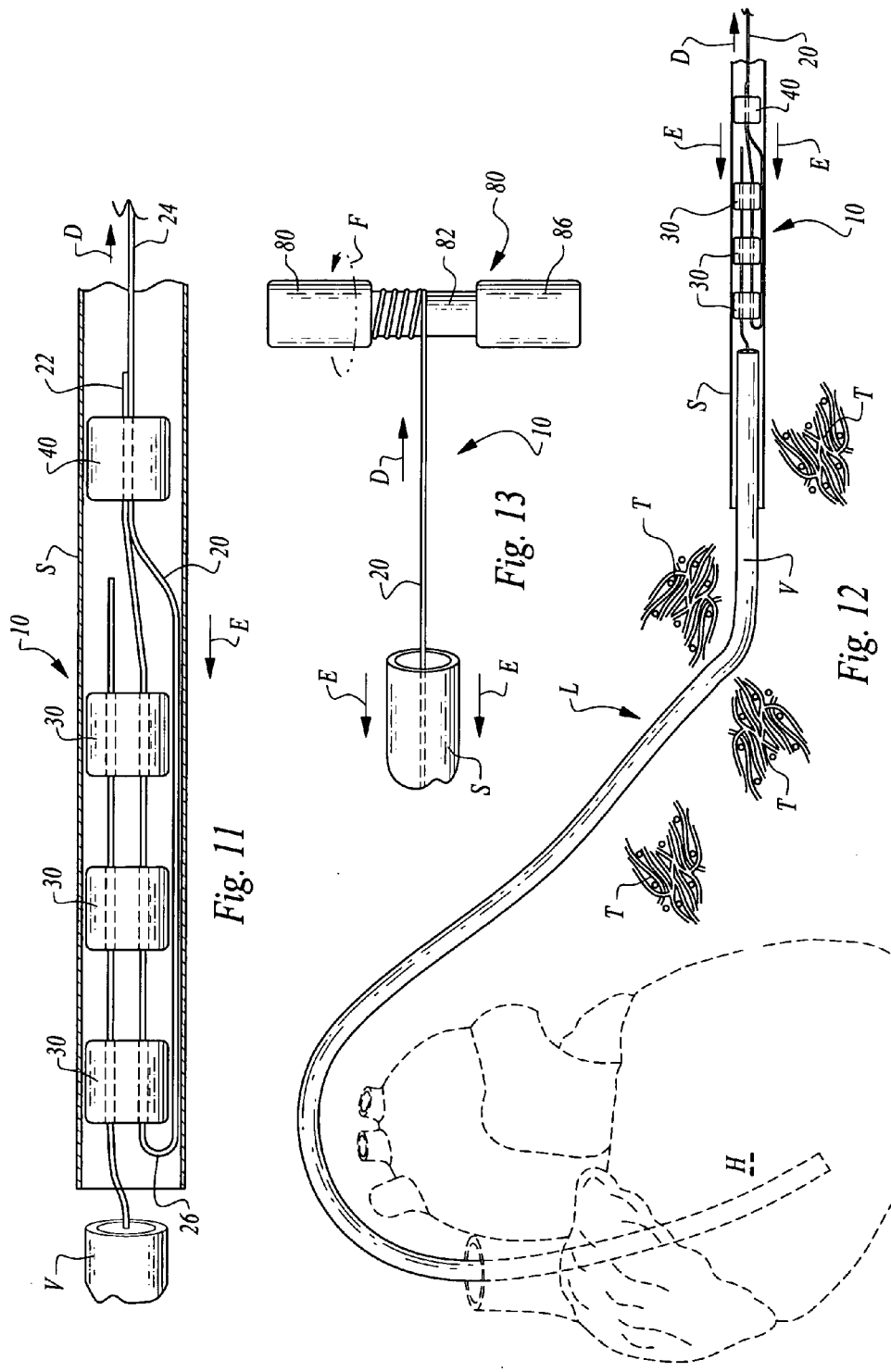

STYLETLESS CARDIAC LEAD EXTRACTION WITH ROLLING TRACTION HANDLE

CROSS-REFERENCE TO RELATED APPLICATIONS

This application claims benefit under Title 35, United States Code §119(e) of U.S. Provisional Application No. 61/271,924 filed on Jul. 28, 2009 and U.S. Provisional Application No. 61/276,372 filed on Sep. 10, 2009.

FIELD OF THE INVENTION

The following invention relates to methods and systems for removal of cardiac leads such as those associated with pacemakers or defibrillators. More particularly, this invention relates to cardiac lead extraction involving advancing of an extraction sheath over the cardiac lead before removal of the lead and systems for tensioning the lead to facilitate extraction sheath advancement, especially tensioning systems which are styletless in nature.

BACKGROUND OF THE INVENTION

Pacemaker or defibrillator leads are becoming increasingly prevalent. Lead extraction is sometimes a necessary procedure for infection, vascular disease or patient preference. Current extraction systems require the use of a locking stylet system in order to remove the pacer or defibrillator lead. The locking stylet provides traction over the lead body, to allow an extraction sheath to be advanced over the length of the lead, on an outer surface thereof, to break up tissue adhering to the lead.

With prior art systems, if a locking stylet cannot be placed within the central lumen of the lead, this usually precludes the extraction of the lead, since traction cannot be produced, and an extraction sheath cannot be effectively inserted over the lead without tensile support. One styletless system is known and manufactured by Cook Medical under the trademark BULLDOG, and described as "lead extender." This system uses the inner core wire by a locking mechanism to form a bond between the lead and a lead extender. This bond formed by the Cook Medical system has limited strength characteristics and can be relatively slow and difficult to employ, thus exemplifying the need for an improved system of styletless lead extraction.

Furthermore, with both stylet based and styletless systems, the metal wire locking stylet or corresponding structure must be held in gloved hands of a medical practitioner and have significant tension applied thereto. This tensioning of the thin metal wire can cause discomfort and fatigue to the operator when placing traction on the wire. Also, it can be difficult to collect slack in such prior art extraction systems, often leading to less than satisfactory looping of the wire around the wrist of the medical practitioner. Accordingly, an improved human interface with the traction wire is needed.

SUMMARY OF THE INVENTION

With this invention a styletless cardiac lead extraction system and method are provided which forms a strong bond with the lead and is easy to configure for use and easy to use to maximize the quality of outcomes during lead extraction procedures. The system generally includes an elongate flexible cord having at least one crimping bead thereon and preferably a plurality of crimping beads. These crimping beads act as a preferred form of clamp that can have different configurations with one or more holes or slots that can receive the elongate flexible cord therein and also one of the wires within the cardiac lead, typically the inner wire thereof. The crimping bead has deformation forces applied thereto, causing the crimping bead to collapse down onto the wire of the cardiac lead. The elongate flexible cord has now been secured to the lead through the inner wire. Tension can then be provided on the cord to facilitate extraction sheath advancement over the lead.

In a most preferred form of the invention, a plurality of crimping beads are provided to maximize support and secure attachment of the crimping beads to the inner wire of the lead. Furthermore, one crimping bead can be provided to crimp the elongate flexible lead back upon itself so that a loop is provided at a proximal end of the elongate flexible lead. The beads and elongate flexible cord are each sized to fit within an interior of the extraction sheath, such as by threading. Thus, the lead can be held in tension through tension on the cord passing through an interior of the extraction sheath as the extraction sheath is advanced in an opposite direction to the tension force, along an outer surface of the lead.

To facilitate holding of the distal end of the cord, a traction handle is preferably provided. This traction handle includes an axle which can have the distal end of the cord attached thereto, either directly to an outer surface of the axle or through a hole passing through the axle. Caps at ends of the traction handle are preferably provided to both provide additional surface for gripping with hands of a user, and preferably coated with a comfortable high friction easy to grip surface. The caps also provide a central area between the caps to keep the slack portions of the cord readily collected upon the traction handle as the lead is extracted and as the extraction sheath is advanced.

OBJECTS OF THE INVENTION

Accordingly, a primary object of the present invention is to provide a system for extracting a cardiac lead that does not require use of a stylet and which can be used when a locking stylet cannot be used.

Another object of the present invention is to provide a lead extraction system which is easy to use and safe.

Another object of the present invention is to provide a lead extraction system which allows for a high strength bond between an extraction cord and the lead itself so that the extraction sheath can be effectively advanced.

Another object of the present invention is to provide a method for cardiac lead extraction that does not require a stylet.

Another object of the present invention is to provide a lead extraction method which is easy and safe to practice.

Other further objects of the present invention will become apparent from a careful reading of the included drawing figures, the claims and detailed description of the invention.

BRIEF DESCRIPTION OF THE DRAWINGS

FIG. 11 is a side elevation view of a cardiac lead and associated wire that have had a system of this invention attached thereto with tension applied to the lead through the central wire within the lead and utilizing the system of this invention to allow for tensioning of the lead, and also showing the extraction sheath being advanced according to the method of this invention.

FIG. 12 is a schematic view similar to that which is shown in FIG. 1, but after attachment of the system of this invention to the wire within the lead and tensioning of the wire, and in the process of advancing the extraction sheath over an exterior surface of the lead prior to lead extraction.

FIG. 13 is a top plan view of a distal end of the extraction sheath, and showing how the elongate flexible cord can be routed over a traction handle and the traction handle can be rotated to gather up slack and apply tension to the lead through the cord and crimping beads defining the system of this invention.

DESCRIPTION OF THE PREFERRED EMBODIMENT

Figure 1:
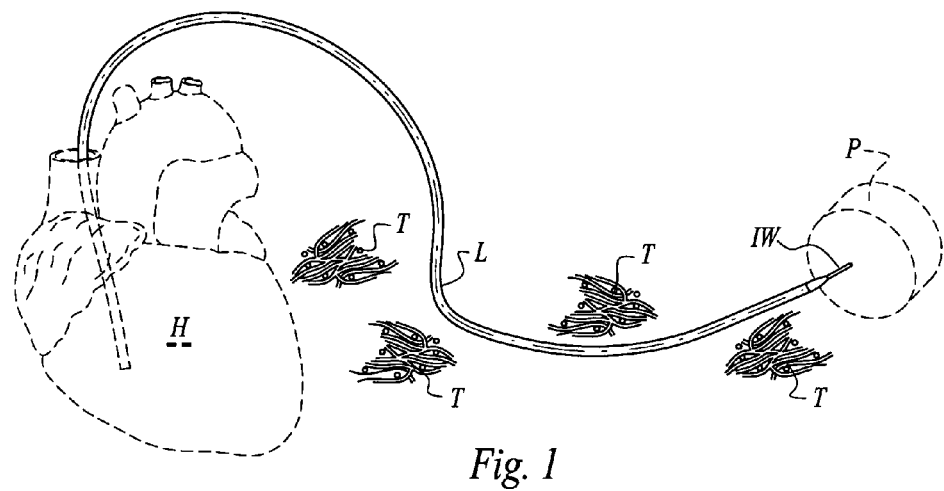
FIG. 1 is a schematic of a lead extending between a heart and a pacemaker or other implanted medical device, before utilizing the system and method of this invention for extraction of the lead from within the patient.

Referring to the drawings, wherein like reference numerals represent like parts throughout the various drawing figures, reference numeral 10 (FIG. 12) is directed to a system for tensioning a cardiac lead L to facilitate advancement of an extraction sheath S over the lead L to separate the lead L from adjacent body tissues T (FIG. 1). The lead L generally extends from a heart H to a pacemaker P or other typically subcutaneous medical device adapted to interact with the heart H or other interior structures.

Figure 2:
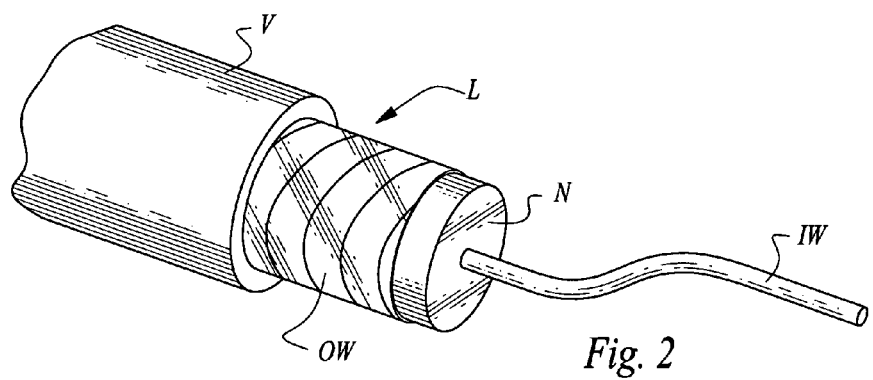
FIG. 2 is a perspective view of a distal end of the lead showing the various parts of the lead, including an inner wire running through a center of the lead which provides a most preferred structure to engage when applying tension for advancing of the extraction sheath and later removal of the lead axially.

The lead L typically includes an outer wire OW and an inner wire IW therein. Typically insulation N is located between the inner wire IW and outer wire OW (FIG. 2). An outer cover V is provided on the lead L (FIG. 2), defining an outermost portion of the lead L which is typically that portion of the lead L which can tend to adhere to bodily tissues T adjacent the implantation site. Separation of the cover V of the lead L from such adhering tissues T is the primary purpose of using the extraction sheath S before lead L removal.

In essence, and with particular reference to FIGS. 3 and 11-13, basic details of the system 10 of this invention and associated method are described, according to a most preferred embodiment. The system 10 includes a cord 20 of elongate flexible form. At least one crimping bead 30, and preferably three or more crimping beads 30 are provided on the cord 20 as a preferred form of clamp for securing to a wire such as the inner wire IW associated with the lead L. Crimping beads include at least one hole or slot into which the inner wire IW or other wire associated with the lead L can be threaded or placed laterally. The crimping bead 30 can then be deformed as it is made out of a deformable material, and complete the process of attaching the cord 20 to the lead L.

Once so attached, tension can be applied to the lead L (along arrow D of FIGS. 11 and 12). This tends to straighten the lead L and allows for advancement of the extraction sheath S axially over the lead L to separate the cover V of the lead L from adjacent tissues T (FIGS. 1 and 12) to facilitate lead L extraction.

Figure 14:
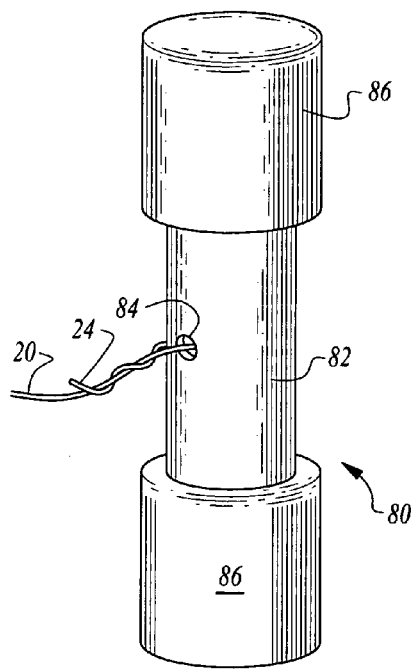
FIG. 14 is a perspective view of the traction handle after initial attachment of the cord thereto.
Figure 15:
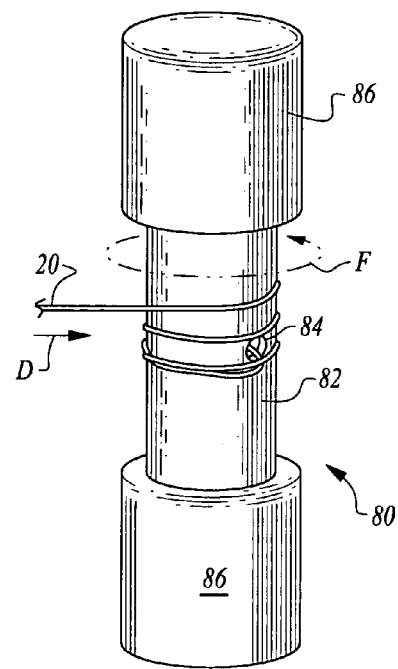
FIG. 15 is a perspective view similar to that shown in FIG. 14 and illustrating the traction handle after it has been rotated a few times to gather up slack and/or readily facilitate customized length of the elongate flexible cord for comfortable application of traction to the lead during advancement of the extraction sheath for lead extraction.

To facilitate gripping the cord 20 to apply tension thereto, a traction handle 80 is preferably provided (FIGS. 13-15). The traction handle 80 is configured so that the cord 20 can be attached thereto and so that the traction handle 80 can be rotated (along arrow F of FIGS. 13 and 15) to gather up slack in the cord 20 and provide a convenient grip for holding and tensioning by a medical practitioner.

Figure 3:
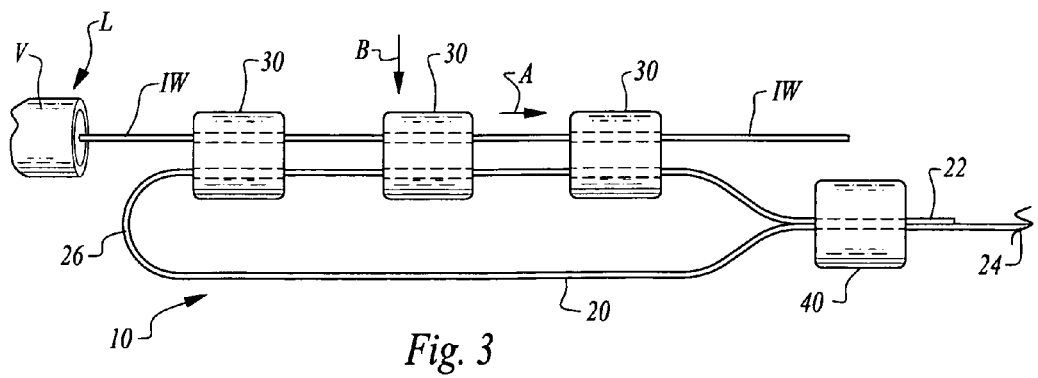
FIG. 3 is a top plan view of the system of this invention after having been coupled to a wire extending from the cardiac lead, and ready for application of tension.

More specifically, and with particular reference to FIGS. 3, 11, 16 and 17, details of the cord 20 are described, according to this preferred embodiment. The cord 20 is an elongate flexible line extending from a proximal end 22 to a distal end 24. The proximal end 22 is that end closest to the lead L and secured to the inner wire IW or other wire within the lead L. Preferably, the cord 20 is formed into a loop 26 adjacent the proximal end 22, such as by crimping the cord 20 back on itself through one of the crimping beads 40 (FIGS. 3, 11 and 12).

The cord 20 is preferably provided with the performance characteristics thereof by selecting the cord 20 from an appropriate material, and secondarily forming the cord 20 to exhibit the performance characteristics desired. The cord 20 is preferably substantially inelastic but flexible. Hence, when tension loads are applied to the cord 20 it does not tend to stretch. However, the cord 20 is preferably highly flexible so that it can bend as required, and especially at a tip of the loop 26 where the cord 20 needs to bend back on itself and still reside within an interior of the extraction sheath S (FIG. 11). The cord 20 is shown with a particular diameter similar to that of the inner wire IW within the lead L. However, the cord 20 could vary in width and other characteristics and still function according to this invention. By crimping the cord 20 back on itself to form the loop 26, forces between the inner wire IW and cord 20 are preferably carried by two or more crimping beads 30 so that forces applied thereto are distributed somewhat evenly.

With particular reference to FIGS. 4-10, details of the crimping beads 30 are described, according to this most preferred embodiment. The crimping beads 30 provide a preferred form of clamp for attaching the cord 20 to the inner wire IW or other wire associated with the lead L. One form of such clamp is a deformable mass, in one form illustrated herein as a crimping bead 30. The crimping bead 30 can be spherical in form, cylindrical in form, or variations thereof as well as other shapes. For simplicity, the crimping beads 30 are shown herein as having a generally standard cylindrical form so that the crimping beads 30 are circular at ends 32 thereof and approximately cylindrical on sides 34 between the ends 32 when viewed laterally.

The crimping beads 30 can be formed of a variety of different materials that have the appropriate crimping characteristics for holding tightly to the inner wire IW or other wire associated with the lead L. Materials that can include such crimpability include aluminum, lead and other materials having a malleable nature. If the materials forming the crimping bead 30 is relatively less deformable, a crimping tool can be utilized to provide a mechanical advantage to the user and effectively crimp the crimping bead so that the intermediate wire LW or other wire associated with the lead L is effectively captured to the cord 20.

Another material which can be crimpable is various different alloys of nickel titanium selected to have a transition temperature so that in the typical operating environment the crimping beads 30 can be readily deformed. One advantage of nickel titanium is its relatively high degree of biocompatability, making it particularly suitable for utilization during medical procedures. However, the crimping beads 30 need not necessarily come into direct contact with the body of a patient, such that highest degrees of biocompatability are not required. Other composite materials designed to have the desired degree of deformabilty can also be provided. As the crimping beads need to fit within the extraction sheath which generally has a diameter close to that of the lead itself, the crimping beads 30 must have a rather small cross-sectional size. The crimping beads 30 can be colored to make them easier to see by a user.

Preferably, the crimping beads 30 are pre-attached to the cord 20, and preferably as a plurality of separate crimping beads 30 (see FIG. 16) to enhance the strength with which the crimping beads 30 are bonded to the cord 20. Pre-attachment eliminates such an attachment step from the tasks that need to be performed by the medical practitioner.

In a most preferred form of the invention, the crimping beads 30 also include a collapsible bore 36 into which the inner wire IW or other wire associated with the lead L can be threaded (along arrow A of FIGS. 3-5) before crimping of the crimping bead 30. This collapsible bore 38 can be collapsed during crimping of the crimping bead 30 to lock the intermediate wire IW to the crimping bead 30. A fixed bore 36 is also provided with this crimping bead 30 which preferably is already pre-affixed to the cord 20.

Alternatively, the crimping beads 30 could be threaded onto the cord 20, but not yet fixed in position. A crimping tool would then be utilized to affix the crimping bead 30 simultaneously to both the cord 20 and the inner wire IW. Such a process is beneficial in that it can facilitate prevention of unwanted slack between sections of the inner wire IW or cord 20 between multiple adjacent crimping beads 30.

Figure 4:
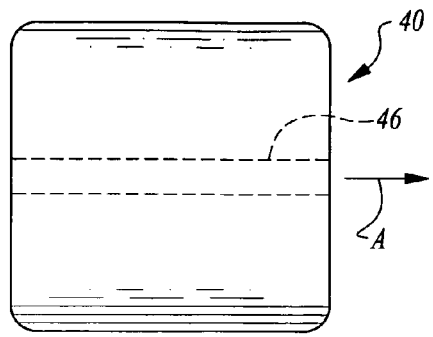
FIG. 4 is a side elevation view of one form of crimping bead according to this invention, illustrating a first alternative embodiment to the preferred embodiment shown in FIG. 3.
Figure 6:
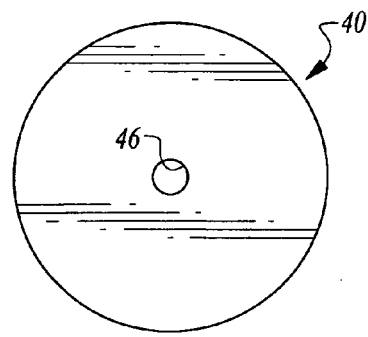
FIG. 6 is an end elevation view of that which is shown in FIG. 4.
Figure 5:
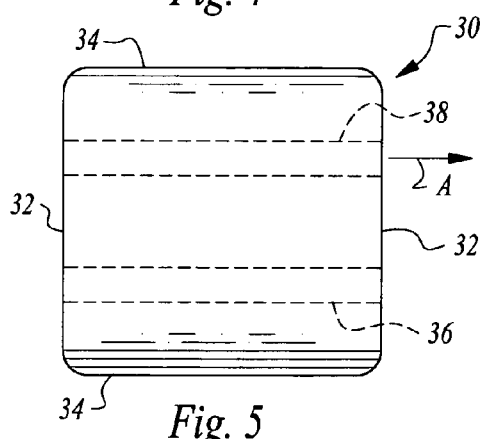
FIG. 5 is a side elevation view similar to that which is show in FIG. 4, but for an embodiment corresponding with the crimping beads as shown in FIG. 3.
Figure 7:
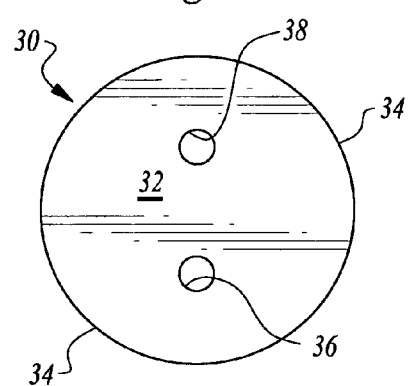
FIG. 7 is an end elevation view of that which is shown in FIG. 5.

Crimping beads 30 of various alternative embodiments could also be provided. For instance, a first alternative crimping bead 40 is shown in FIGS. 4-6. In this alternative, a single combined bore 46 is provided. The cord 20 and inner wire IW would be routed through this single combined bore 46 before crimping of the crimping bead 40 to secure the cord 20 and inner wire IW together within the crimping bead 40. Such a first alternative crimping bead 40 can also be utilized to secure a proximal end 22 of the cord 20 to a distal end 24 of the cord 20 or intermediate portion of the cord 20 to form the loop 26, and effectively crimp the cord 20 back on itself (FIGS. 3, 11 and 12).

Figure 8:
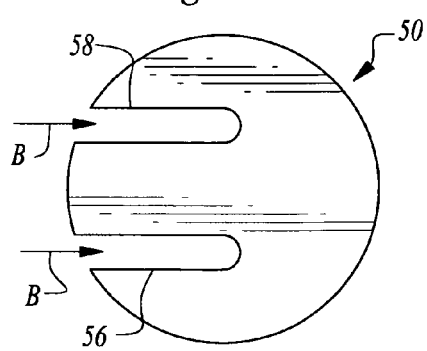
FIG. 8 is a front elevation view of a second alternative crimping bead including a pair of slots therein. One of the slots is configured to receive the elongate flexible cord while the other slot is configured to receive a portion of the wire of the cardiac lead therein.

A second alternative crimping bead 50 is shown in FIG. 8. In this embodiment, a first slot 56 and second slot 58 are provided. The cord 20 would be provided in one of the slots 56, 58, in a lateral sliding motion (along arrow B of FIGS. 3 and 8-10). The other slot 58, 56 would receive the inner wire IW or other wire associated with the lead L. The crimping bead 50 would then be crimped to close the slots 56, 58 and capture the cord 20 and inner wire IW to the crimping bead 50.

Figure 9:
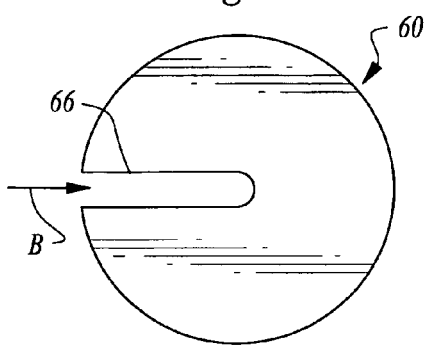
FIG. 9 is an elevation view of a third alternative crimping bead having a single slot therein, the single slot configured to simultaneously receive both the elongate flexible cord and the wire associated with the lead being extracted.

In FIG. 9 a third alternative crimping bead 60 is shown having a single combined slot 66. Both the cord 20 and inner wire IW could be routed into this single combined slot 66. Upon crimping of this crimping bead 60, the cord 20 and inner wire IW would be securely attached together.

Figure 10:
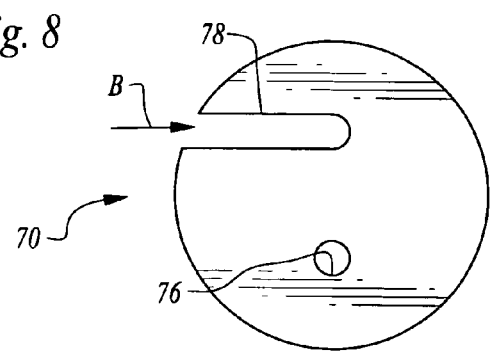
FIG. 10 is an end elevation view of a fourth alternative crimping bead exhibiting both a slot and a hole. The hole would typically be pre-affixed with the elongate flexible cord therein, and the slot would receive the wire associated with the cardiac lead therein prior to application of impression forces crimping the crimping bead on the wire associated with the cardiac lead.
Figure 16:
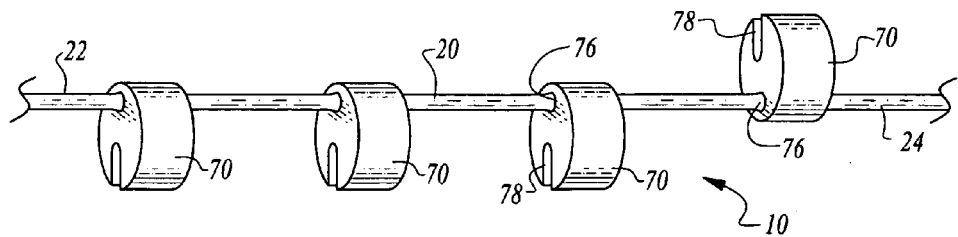
FIG. 16 is a perspective view of the portion of the cord with the crimping beads shown thereon and before being used to attach to a wire associated with the lead.
Figure 17:
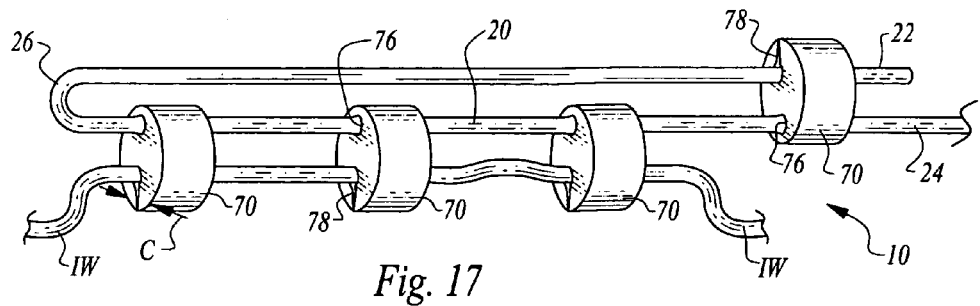
FIG. 17 is a perspective view similar to that which is shown in FIG. 16 but after placement of the wire associated with the lead into slots in the crimping beads and after an additional crimping bead has been used to seal the cord back on itself to form a loop.

In FIGS. 10, 16 and 17 a fourth alternative crimping bead 70 is shown. With this crimping bead 70, a fixed bore 76 is provided as well as a slot 78. The fixed bore 76 can have the cord 20 affixed therein or the cord 20 pre-threaded through the fixed bore 76 but able to slide initially within the fixed bore 76. The slot 78 is provided open on an edge of the crimping bead 70 to allow for sliding insertion of the inner wire IW or other wire associated with the lead L (such as along arrow B of FIGS. 3 and 8-10). Such sliding of the inner wire IW into a slot 78 within the crimping bead 70, is also shown in FIG. 17.

Furthermore, such a configuration for the crimping bead 70 can simplify the process of attaching the system 10 of this invention to an inner wire IW or other wire associated with the lead L, when the crimping beads 70 are particularly small so that they can fit within a particularly small extraction sheath S. Especially if the crimping bead 70 is somewhat cylindrical in shape, it can be held in fingers of a user and the curving side wall can be felt. The inner wire IW can be brought laterally up to the crimping bead 70 and the crimping bead rotated within fingers of the user with the inner wire IW adjacent the crimping bead 70. When the slot 78 in the crimping bead 70 is aligned with the inner wire IW, the inner wire IW will fall down into the slot 78 and be held therein.

By forming the slot 78 slightly off line from a center line of the crimping bead 70, such rolling of the crimping bead 70 in one direction will tend to capture the inner wire IW as the slot 78 comes into alignment with the inner wire IW, to further simplify this attachment process, even when the crimping bead 70 and slot 78 might be difficult for the medical practitioner to see visually. Once the wire IW has been inserted into the slot 78, the bead 70 is compressed (along arrow C of FIG. 17) to secure the cord 20 to the wire IW.

With particular reference to FIGS. 13-15, particular details of the traction handle 80 are described, according to this preferred embodiment. The traction handle 80 is configured to be attached to the distal end 24 of the cord 20 to allow a medical practitioner to easily handle and apply tension to the cord 20, and thus the lead L through the inner wire IW or other wire associated with the lead L. The traction handle 80 preferably includes an elongate axle 82 about which the distal end 24 of the cord 20 can be wrapped. To facilitate securing of this distal end 24 of the cord 20 to the axle 82, a hole 84 can be provided passing radially through the axle 82, and through which the distal end 24 of the cord 20 can be threaded for initial attachment of the distal end 24 of the cord 20 to the axle 82 of the traction handle 80. Thereafter, the traction handle 80 can be rotated (along arrow F of FIGS. 13 and 15) to take up slack in the cord 20. Preferably, the distal end 24 of the cord 20 is first wrapped about itself a little to prevent pulling out of the cord 20 relative to the traction handle 80.

Caps 86 are preferably provided on ends of the traction handle 80 to further enhance a gripability of the traction handle 80, especially when the caps 86 are formed of an at least partially deformable material. These caps 86 also tend to keep the cord 20 aligned within a central portion of the axle 82.

Once slack has been gathered, tension (along arrow D of FIG. 13) can be applied by the medical practitioner gripping the traction handle 80 and tensioning it away from the lead L. The cord 20 will have already been threaded through the interior of the extraction sheath S. The extraction sheath S can then be advanced (along arrow E of FIGS. 11-13) axially over the lead L while tension is applied to the lead L through the cord 20 and traction handle 80. Extraction sheath S advancement can continue, separating body tissues T from the cover V of the lead L. Once the extraction sheath S has advanced sufficiently far along the lead L, the lead L has been freed up from adjacent tissues T and can be carefully axially removed by the medical practitioner.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A cardiac lead extraction system, comprising in combination:
    a cardiac lead;
    an elongate flexible cord;
    an elongate extraction sheath;
    said cord sized to fit inside said extraction sheath;
    at least one clamp;
    said clamp adapted to be attached to said elongate flexible cord;
    said clamp adapted to be attached to a cardiac lead wire, wherein the cardiac lead wire is within the cardiac lead;
    said clamp sized to fit inside the extraction sheath and travel relative to said extraction sheath; and
    wherein said clamp includes a deformable mass adapted to be deformed onto the cardiac lead wire to secure said clamp to the wire when so deformed.

2. The system of claim 1 wherein said clamp is in the form of a crimping bead, said crimping bead having at least one opening for receiving the cardiac lead wire therein.

3. The system of claim 2 wherein said crimping bead includes a single hole, said single hole sized to receive both said elongate flexible cord passing therethrough and the cardiac lead wire, each threaded through said single hole, said crimping bead adapted to be deformed sufficiently to cause said crimping bead to secure said elongate flexible cord to the wire.

4. The system of claim 2 wherein said crimping bead includes at least two holes passing therethrough, with one of said holes pre-affixed to said elongate flexible cord passing therethrough, and one of said at least two holes initially open for receiving the cardiac lead wire threaded therethrough.

5. The system of claim 2 wherein said crimping bead includes at least two slots, each of said slots adapted to receive either said elongate flexible cord therein or the cardiac lead wire therein, each of said slots adapted to be closed by crimping of said crimping bead.

6. The system of claim 1 wherein said at least one clamp includes a plurality of clamps spaced from each other, each of said clamps pre-affixed to said elongate flexible cord, and each of said plurality of clamps adapted to be attached to the cardiac lead wire.

7. The system of claim 1 wherein a traction handle is provided, said traction handle sized to be gripped in a hand of a user, said traction handle adapted to be coupled to a distal end of said elongate flexible cord opposite a proximal end of said elongate flexible cord, said at least one clamp located closer to said proximal end of said elongate flexible cord than to said distal end.

8. The system of claim 7 wherein said traction handle includes an elongate axle sized to be grasped within a palm of a hand, said axle including a hole passing therethrough, said hole sized to allow said elongate flexible cord to be routed therethrough for securing of said elongate flexible cord to said traction handle, said traction handle adapted to be rotated within a hand of a user to cause said elongate flexible cord to be wound on said axle and take up excess length of said elongate flexible cord, while maintaining tension on said elongate flexible cord, such as during advancing of said extraction sheath over the cardiac lead to separate the cardiac lead from body tissues adjacent thereto for cardiac lead extraction.

9. A cardiac lead extraction system, comprising in combination:
    a cardiac lead;
    an elongate flexible cord;
    an elongate extraction sheath;
    said cord sized to fit inside said extraction sheath;
    at least one clamp;
    said clamp adapted to be attached to said elongate flexible cord;
    said clamp adapted to be attached to a cardiac lead wire, wherein the cardiac lead wire is within the cardiac lead;
    said clamp sized to fit inside the extraction sheath and travel relative to said extraction sheath; and
    wherein said clamp includes a deformable mass adapted to be deformed onto the cardiac lead wire to secure said clamp to the wire when so deformed;
    wherein said clamp is in the form of a crimping bead, said crimping bead having at least one opening for receiving the cardiac lead wire therein; and
    wherein said crimping bead includes a hole and a slot, said hole having said cord pre-affixed therein, said slot sized to allow the cardiac lead wire to slide laterally into said slot, said crimping bead adapted to be crimped to close said slot about the wire to hold the wire within said slot.

* * * * *